United States Patent [19]
Posner et al.

[11] Patent Number: 5,925,526
[45] Date of Patent: Jul. 20, 1999

[54] ANTIGEN RECOGNIZED BY PATIENTS WITH ANTIBODY ASSOCIATED CEREBELLAR DEGENERATION, DNA ENCODING SAME AND USES THEREOF

[75] Inventors: Jerome B. Posner; Henry M. Furneaux, both of New York, N.Y.

[73] Assignee: Sloan-Kettering Institute for Cancer Research, New York, N.Y.

[21] Appl. No.: 08/478,609

[22] Filed: Jun. 7, 1995

Related U.S. Application Data

[62] Division of application No. 08/427,993, Apr. 24, 1995, Pat. No. 5,668,013, which is a continuation of application No. 07/646,292, Jan. 25, 1991, abandoned.

[51] Int. Cl.$^6$ .......................... G01N 33/53; G01N 33/536
[52] U.S. Cl. .......................... 435/7.1; 435/7.23; 435/7.72; 435/7.9; 435/7.92; 436/518; 436/536; 436/544; 436/545; 436/546; 436/804
[58] Field of Search ..................... 435/7.1, 7.23, 435/7.9, 7.72, 7.92; 436/536, 544, 545, 546, 804, 518

[56] References Cited

U.S. PATENT DOCUMENTS 4,569,794  2/1986  Smith et al.

OTHER PUBLICATIONS

Harlow and Lane, "Antibodies a Laboratory Manual", published by Cold Spring Harbor Laboratory, see pp. 562–564 and 551–561, 1988.

Anderson, N.E., et al. (1988) "Autoantibodies in paraneoplastic syndromes associated with small–cell lung cancer." *Neurology* 38: 1391–1398.

Anderson, N.E., et al. (1988) "A variant of the anti–Purkinje cell antibody in a patient with paraneoplastic cerebellar degeneration." *Neurology* 38: 1018–1026.

Brain, L. and Wilkinson, M. (1965) "Subacute cerebellar degeneration associated with neoplasms." *Brain* 88: 465–478.

Darnell, R., et al. (1989) "Characterization of neural antigens recognized by autoantibodies in CSF and serum of a patient with cerebellar degeneration: co–expression in Purkinje cells and tumor lines of neuroectodermal origin." *Neurology* 39 (Supp.1): 385.

Furneaux, H.M., et al. (1990) "Selective expression of Purkinje cell antigens in tumor tissue from patients with paraneoplastic cerebellar degeneration." *New Eng. J. Med.* 322: 1844–1851.

Gentz, R., et al. (1989) "Parallel Association of Fos and Jun leucine zippers juxtaposes DNA binding domains." *Science* 243: 1695–1699.

Greenlee, J.E., et al. (1983) "Antibodies to cerebellar Purkinje cells in patients with paraneoplastic cerebellar degeneration and ovarian carcinoma." *Annals of Neurology* 6: 609–613.

Jaeckle, K.A., et al. (1988) "Autoimmune response of patients with paraneoplastic degeneration to a Purkinje cell cytoplasmic antigen." *Annals of Neurology* 18: 592–600.

Janson, J.–C. (1984) "Large–scale affinity purification–state of the art and future prospects." *Trends in Biotechnology* 2: 31–38.

Lampson, L. (1987) "Molecular bases of the immune response to neural antigens." *Trends Neurosci.* 10: 211–216.

Rodriguez, M., et al. (1988) "Autoimmune paraneoplastic cerebellar degeneration: ultrastructural localization of antibody–binding sites in Purkinje cells." *Neurology* 38: 1380–1386.

Vinson, C., et al. (1989) "Scissors–grip model for DNA recognition by a family of leucine zipper proteins." *Science* 246: 911–916.

Young, R.A. and Davis, R.W. (1983) "Efficient isolation of genes by using antibody probes." *Proc. Natl. Acad. Sci., USA* 90: 1194–1198.

*Primary Examiner*—Anthony C. Caputa
*Attorney, Agent, or Firm*—John P. White; Cooper & Dunham LLP

[57] ABSTRACT

An isolated nucleic acid sequence encoding major Yo paraneoplastic antigenic polypeptide is provided by this invention. This invention also provides a purified major Yo antigenic polypeptide and compositions containing the purified major Yo antigenic polypeptide. Further provided by this invention is a monoclonal antibody directed to an epitope on the major Yo paraneoplastic antigenic polypeptide. Compositions containing this monoclonal antibody also are provided by this invention. This invention also provides methods of diagnosis and treatment using the compositions described hereinabove.

6 Claims, 10 Drawing Sheets

```
                    20                         40                         60
                    *                          *                          *
SAAGPNGAEAAQRSLGGGAS     RPRAALAEGGGAGEEPGAAA     EAGRRRGPLPLEDPAEMLAE 80                        100                        120
                    *                          *                          *
NLVEEFEMKEDEPWYDHQDL     QQDLQLAAELGKTLLDRNTE     LEDSVQQMYTTNQEQLQEIE

>LEUZIP
                                                            |
                   140                        160           |           180
                    *                          *            |            *
YLTKQVELLRQMNEQHAKVY     EQLDVTARELEETNQKLVAD     SKASQQKILSLTETIECLQT
                                                              ●                ●

200                        220                        240
                    *                          *                          *
NIDHLQSQVEELKSSGQGRR     SPGKCDQEKPAPSFACLKEL     YDLRQHFVYDHVFAEKITSL
     ●        ●

260                        280                        300
                    *                          *                          *
QGQPSPDEEENEHLKKTVTM     LQAQLSLERQKRVTMEEEYG     LVLKENSELEQQLGATGAYR 320                        340                        360
                    *                          *                          *
ARALELEAEVAEMRQMLQSE     HPFVNGVEKLVPDSLYVPFK     EPSQSLLEEMFLTVPESHRK 380                        400                        420
                    *                          *                          *
PLKRSSSETILSSLAGSDIV     KGHEETCIRRAKAVKQRGIS     LLHEVDTQYSALKVKYEELL 440                        460                        480
                    *                          *                          *
KKCQEEQDSLSHKAGRPPGC     SQGPDWSDAQSEPVASGWEL     ASVNPEPVSSPTTPPEYKAL

500
                    *
FKEIFSCIKKTKQEIDEQRT     KYRSLSSHS
```

FIG. 7A

```
                   20                     40                     60
                    *                      *                      *
TCCCCGCAAGATCTTCAACT TGCTGCTGAGCTTGGGAAGA CATTACTGGATCGGAACACA
 S  P  Q  D  L  Q  L  A  A  E  L  G  K   T  L  L  D  R  N  T>

80                    100                    120
                    *                      *                      *
GAGTTGGAGGACTCTGTTCA GCAGATGTATACAACCAATC AGGAGCAGTTACAGGAAATT
 E  L  E  D  S  V  Q  Q  M  Y  T  T  N   Q  E  Q  L  Q  E  I>

140                    160                    180
                    *                      *                      *
GAGTATCTGACGAAGCAAGT GGAACTTCTACGGCAGATGA ACGAACAACATGCAAAGGTT
 E  Y  L  T  K  Q  V  E  L  L  R  Q  M   N  E  Q  H  A  K  V>

200                    220                    240
                    *                      *                      *
TATGAACAATTAGACGTCAC AGCAAGGGAACTGGAAGAAA CAAATCAAAAGCTAGTTGCT
 Y  E  Q  L  D  V  T  A  R  E  L  E  E   T  N  Q  K  L  V  A>

260                    280                    300
                    *                      *                      *
GACAGCAAGGCCTCACAGCA AAAGATTCTGAGCCTGACTG AAACGATTGAATGCCTGCAA
 D  S  K  A  S  Q  Q  K  I  L  S  L  T   E  T  I  E  C  L  Q>

320                    340                    360
                    *                      *                      *
ACCAACATTGATCACCTCCA GAGCCAAGTGGAGGAGCTGA AGTCATCTGGCCAAGGGAGA
 T  N  I  D  H  L  Q  S  Q  V  E  E  L   K  S  S  G  Q  G  R>

380                    400                    420
                    *                      *                      *
AGGAGCCCGGGAAAGTGTGA CCAGGAGAAACCGGCACCCA GCTTTGCATGTCTGAAGGAG
 R  S  P  G  K  C  D  Q  E  K  P  A  P   S  F  A  C  L  K  E>

440                    460                    480
                    *                      *                      *
CTGTATGACCTCCGCCAACA CTTCGTGTATGATCATGTGT TCGCTGAGAAGATCACTTCC
 L  Y  D  L  R  Q  H  F  V  Y  D  H  V   F  A  E  K  I  T  S>

500                    520                    540
                    *                      *                      *
TTGCAAGGTCAGCCAAGCCC TGATGAAGAGGAAAATGAGC ACTTGAAAAAAACAGTGACA
 L  Q  G  Q  P  S  P  D  E  E  E  N  E   H  L  K  K  T  V  T>

560                    580                    600
                    *                      *                      *
ATGTTGCAGGCCCAGCTGAG CCTGGAGCGGCAGAAGCGGG TGACTATGGAGGAGGAATAT
 M  L  Q  A  Q  L  S  L  E  R  Q  K  R   V  T  M  E  E  E  Y>
```

FIG. 7B

```
                     620                          640                          660
                      *                            *                            *
GGGCTCGTGTTAAAGGAGAA      CAGTGAACTGGAGCAGCAGC      TGGGGGCCACAGGTGCCTAC
 G   L   V   L   K   E   N    S   E   L   E   Q   Q    L   G   A   T   G   A   Y>

680                          700                          720
                      *                            *                            *
CGAGCACGGGCGCTGGAACT      AGAGGCCGAGGTGGCAGAGA      TGCGACAGATGTTGCAGTCA
 R   A   R   A   L   E   L    E   A   E   V   A   E    M   R   Q   M   L   Q   S>

740                          760                          780
                      *                            *                            *
GAGCATCCATTTGTGAATGG      AGTTGAGAAGCTGGTGCCAG      ACTCTCTGTATGTTCCTTTC
 E   H   P   F   V   N   G    V   E   K   L   V   P    D   S   L   Y   V   P   F>

800                          820                          840
                      *                            *                            *
AAAGAGCCCAGCCAGAGCCT      GCTGGAAGAGATGTTCCTGA      CTGTGCCGGAATCACATAGA
 K   E   P   S   Q   S   L    L   E   E   M   F   L    T   V   P   E   S   H   R>

860                          880                          900
                      *                            *                            *
AAGCCTCTCAAGCGCAGCAG      CAGTGAGACGATCCTCAGCA      GCTTGGCAGGGAGTGACATC
 K   P   L   K   R   S   S    S   E   T   I   L   S    S   L   A   G   S   D   I>

920                          940                          960
                      *                            *                            *
GTGAAGGGCCACGAGGAGAC      CTGCATCAGGAGGGCCAAGG      CTGTGAAACAGAGGGGCATC
 V   K   G   H   E   E   T    C   I   R   R   A   K    A   V   K   Q   R   G   I>

980                         1000                         1020
                      *                            *                            *
TCCCTTCTGCACGAAGTGGA      CACGCAGTACAGCGCCCTGA      AGGTGAAGTATGAAGAGTTG
 S   L   L   H   E   V   D    T   Q   Y   S   A   L    K   V   K   Y   E   E   L>

1040                         1060                         1080
                      *                            *                            *
CTGAAGAAGTGCCAAGAGGA      ACAGGACTCCCTGTCACACA      AGGCTGGCAGACCTCCAGGC
 L   K   K   C   Q   E   E    Q   D   S   L   S   H    K   A   G   R   P   P   G>

1100                         1120                         1140
                      *                            *                            *
TGCAGCCAAGGACCTGACTG      GAGTGACGCCCAGTCTGAGC      CTGTTGCCAGCGGCTGGGAA
 C   S   Q   G   P   D   W    S   D   A   Q   S   E    P   V   A   S   G   W   E>

1160                         1180                         1200
                      *                            *                            *
CTGGCCTCTGTCAACCCAGA      GCCCGTGAGTTCCCCTACAA      CACCTCCAGAATACAAAGCG
 L   A   S   V   N   P   E    P   V   S   S   P   T    T   P   P   E   Y   K   A>
```

FIG. 7C

```
                1220                      1240                      1260
                 *                         *                         *
TTGTTTAAGGAGATCTTTAG      TTGCATCAAGAAAACTAAGC      AGGAAATAGATGAACAGAGA
 L  F  K  E  I  F  S       C  I  K  K  T  K         Q  E  I  D  E  Q  R>

1280                      1300                      1320
                 *                         *                         *
ACAAAATACCGATCACTCTC      CTCTCATTCTTAATTGACCT      CTAGCTCTACTACTAATTTG
 T  K  Y  R  S  L  S       S  H  S>

1340                      1360                      1380
                 *                         *                         *
CCTATTGCCTATCGCCTCTC      TCCCATTCAGACAAGTGTTT      GTAGACTCTGAAGCCTAATG 1400                      1420                      1440
                 *                         *                         *
TTACTCATGACGTTTGCCTC      ATTGCTTTGCTTATTTAGCA      AATGCATACAACGAGGAAAG 1460                      1480                      1500
                 *                         *                         *
GAGGTGGCTAGTGGTATCAG      TTCTCTGATCCACTTCCATT      TAACCTCCCCAGGAAATCCC 1520                      1540                      1560
                 *                         *                         *
ATGACAAACTGGCCTCTGGC      TGGCGCGCTGATTAGACTTC      AGTTCCTGAAAAGGACCAGT 1580                      1600                      1620
                 *                         *                         *
GGAGGGAAGAGCTATACTTC      TGGAGAAGTAGGCCTGGAGT      TACTACAGTATGGGGGAAAA 1640                      1660                      1680
                 *                         *                         *
GGGTCGAGTTAGAACAAAGC      TAAGGCAATTCCTATTGCTT      CCTTGCGCAACTTCTCAAAA 1700                      1720                      1740
                 *                         *                         *
CGATGAAAGTCAGAAGGCTG      TCAAACTCAAATATCTTTGC      AAACACTGTTTGAATACTGT 1760                      1780                      1800
                 *                         *                         *
GAATTCTTCATTACGAAGAA      TGTTCGAGAGAAAGCAGGGG      TCTAATCCAAAAGAAATGTC 1820                      1840                      1860
                 *                         *                         *
ATTAACCAATACTCCAAGTC      CTTGAGTTTTGTTATATCTG      AACTAGTTGAACTGTGACTG
```

FIG. 7D

```
                  1880                       1900                      1920
                    *                          *                         *
        ACAGGTAATCCTAATATATC      CAAATCCAACTGAATACCAA    ATTGAGATGGCAAATTTTTG 1940                       1960                      1980
                    *                          *                         *
        TTTGATATAAGTTAGCTTGT      TAGCATATGCCCTAGAGGGC    CTCCATCCCTGATTCTAATG 2000                       2020                      2040
                    *                          *                         *
        TTTTTACTCAAAGCTCTAGC      CTTTAGGATAGGTGAATATG    TAAATCTTTTATCACTTTCT 2060                       2080                      2100
                    *                          *                         *
        CAAATTCAAACTAAAGGGGA      AAGATCAAACCCCTTCCCTT    CCTACCTGTTTTCTGAGCTG 2120                       2140                      2160
                    *                          *                         *
        GCTGACTTGCCAGCCACAAG      CTGCTCTTGCAGAGTTCTTA    CCATTCCTGTAAATGTTTTG 2180                       2200                      2220
                    *                          *                         *
        ACTTGTTGCAGAAATTCCTA      TCTACTTTATTAAGCAGTAT    TGATCTGACTGTGGAAACAT 2240                       2260                      2280
                    *                          *                         *
        CCTCTCACTTGCATTCTTTT      AACTTAAAACTATTTAAGAA    CTGATGTTCCGATTATTGTA 2300                       2320
                    *                          *
        TATATTTTTCTAAAAACCAA      ATAAAGCTACCTATGAAAGG    AATTCCGGAATTC
```

ANTIGEN RECOGNIZED BY PATIENTS WITH ANTIBODY ASSOCIATED CEREBELLAR DEGENERATION, DNA ENCODING SAME AND USES THEREOF

This application is a divisional application of U.S. Ser. No. 08/427,993, filed Apr. 24, 1995, now issued as U.S. Pat. No. 5,668,013, which is a continuation of U.S. Ser. No. 07/646,292, filed Jan. 25, 1991, now abandoned.

This invention was made with support under Grant Number GA08748 from the national Institute of Health. Accordingly, the United States government has certain rights to the invention.

BACKGROUND OF THE INVENTION

Throughout this application various references are referred to within parentheses. Disclosures of these publications in their entirety are hereby incorporated by reference into this application to more fully describe the state of the art to which this invention pertains. Full bibliographic citations for these references maybe found at the end of this application, immediately preceding the claims.

Paraneoplastic cerebellar degeneration (PCD) is a disorder of the cerebellum found in association with neoplasms usually of lung, ovary, breast, or Hodgkins disease. [1] Neuropathological analysis of the affected brains has revealed extensive loss of Purkinje cells, variable loss of granule and basket neurons and proliferation of Bergman glia. [2] The mechanistic relationship between the primary tumor and the resultant cerebellar dysfunction is not clearly understood. The presence of infiltrating lymphocytes in some of the affected brain has suggested an immune mechanism. [3]

A clinically definable subset of patients with paraneoplastic cerebellar degeneration harbor a characteristic antibody which has been call anti-Yo [4]. These sera react with antigens expressed in the Purkinje cells of the normal cerebellum and in the tumor tissue of the affected individual [5]. There is also evidence of increased antibody synthesis in the affected brain. [6] These observations suggest a model for the neurological dysfunction in which an immune response primarily directed against a tumor antigen is misdirected against similar antigens peculiar to the cerebellum. On Western blot analysis of Purkinje cells and tumor tissue, the anti-Yo sera react with at least two antigens, a major species of 62 kd (CDR 62) and a minor species of 34 kd (CDR 34). [7] Anti-Yo antibody has been detected in patients prior to discovery of the tumor. [19]. In four of these patients, prior radiological investigations had disclosed minor abnormalities of uncertain significance. Detection of this antibody prompted surgical exploration and biopsy disclosed a tumor in each case.

The gene encoding the minor antigen (CDR 34) has been isolated and characterized [8,9]. In addition, a cDNA encoding a 52-kd protein has been isolated, recognized by an antineuronal cell antibody in serum from a patient with PCD associated with uterine carcinoma. [18] However, specificity of reaction between the protein encoded by this isolated cDNA and Yo sera was not established. [18]

SUMMARY OF THE INVENTION

An isolated nucleic acid sequence encoding major Yo paraneoplastic antigenic polypeptide is provided by this invention. This invention also provides a purified major Yo antigenic polypeptide and compositions containing the purified major Yo antigenic polypeptide.

A method of detecting an antibody associated with paraneoplastic cerebellar degeneration (PCD) is provided by this invention. This method comprises contacting a suitable sample with the purified major Yo antigenic polypeptide labelled with a detectable marker under conditions so as to form a complex between the purified major Yo antigenic polypeptide and the antibody, detecting the presence of any complex so formed, thereby detecting an antibody associated with paraneoplastic cerebellar degeneration.

Also provided by this invention is a method of determining whether a patient exhibiting neurological symptoms has paraneoplastic cerebellar degeneration (PCD) or harbors a tumor expressing major Yo antigen, which comprises contacting a suitable sample from the patient with the major Yo antigenic polypeptide, the polypeptide being labeled with a detectable marker, under suitable conditions so as to form a complex between the antibody and the polypeptide, detecting the presence of any complex so formed, the presence of complex being a positive determination that the patient has a tumor which expresses a major Yo antigen or PCD.

A method of inhibiting the proliferation of neoplastic cells in a patient having paraneoplastic cerebellar degeneration (PCD) also is provided by this invention. This method comprises administering to the patient an effective amount of a monoclonal antibody directed to the major Yo paraneoplastic antigenic polypeptide, the monoclonal antibody being labeled with a therapeutic agent, in an amount which is effective to inhibit the proliferation of the neoplastic cells, thereby inhibiting the proliferation of neoplastic cells in a patient having PCD.

This invention further provides a method of imaging neoplastic cells in a patient, wherein the neoplastic cells are associated with paraneoplastic cerebellum degeneration (PCD), which comprises administering to the patient an effective amount of a monoclonal antibody directed to major Yo paraneoplastic antigen, the monoclonal antibody being labelled with an imaging agent, under conditions to form a complex between the monoclonal antibody and an antigenic polypeptide associated with PCD, imaging any complex so formed, thereby imaging neoplastic cells in a patient.

BRIEF DESCRIPTION OF THE FIGURES

FIG. 1—Epitope selection analysis of pY1, pY2. Nitrocellulose filters containing fusion protein encoded by pY1, pY2 and as a control a β-galactosidase—ovalbumin fusion protein were incubated with anti Yo sera (5 μ/ml) for 2 hours at room temperature. After washing with TBST, the IgG fraction bound to the filter was eluted with 1.0M Na Citrate (pH 2.5). The purified IgG was then re-reacted with Western blot nitrocellulose strips containing protein from human Purkinje cells. Lane 1, negative contral eluate from ovalbumin fusion protein. Lane 2 eluate from pY1. Lane 3 eluate from pY2.

(A) Protein extracts (50 μg total protein) from pBS (parental plasmid containing no insert) and pY2 were resolved by SDS 10% Acrylamide gel electrophoresis, transferred to nitrocellulose and incubated with anti Yo sera (lanes 1,2).

(B) The fusion protein encoded by pY2 was purified by preparative SDS—10% acrylamide gel electrophoresis.

The partially purified protein was then run on a "curtain well" SDS-polyacrylamide gel, transferred to nitrocellulose and cut into strips of equal size. Strips (containing equal amounts of fusion protein) were then incubated with lane 1, normal human sera, lanes 2, 3, 4, 5 anti Yo positive sera and lanes 6–10 anti Yo negative sera.

Figure 4:
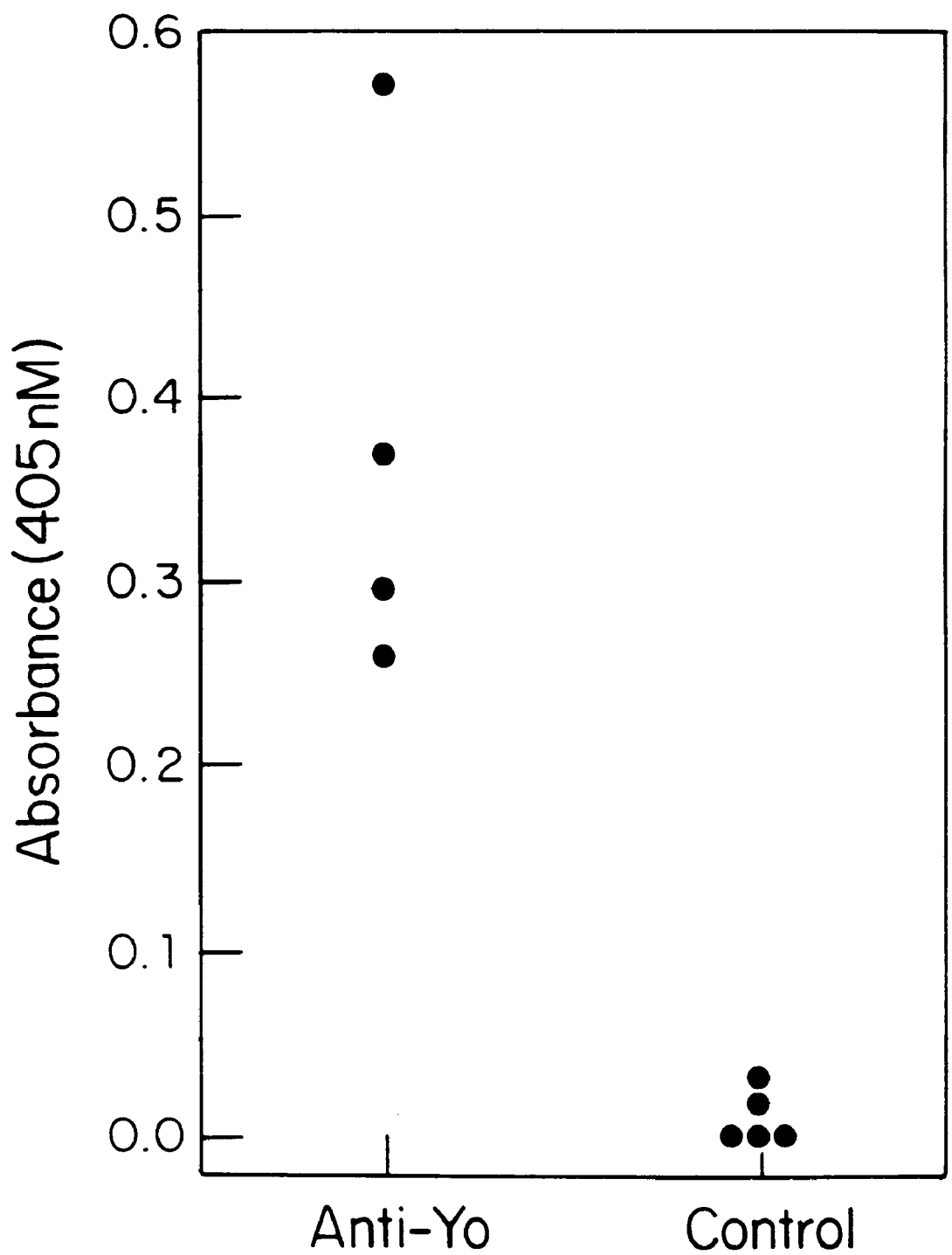

FIG. 4—Elisa Assay using pY2 Fusion Protein Partially purified pY2 fusion protein was immobilized to 96 well microtitre plates and serum reactivity assayed as described in materials and methods. Each dot on the two Y axes correspond to a single determination.

FIG. 5—The composite open reading frame specified by pY1 pY2 is shown in single letter amino acid code. The leucine zipper domain is shown and the participating leucine residues highlighted. Seq. ID NO. 1.

Figure 6:
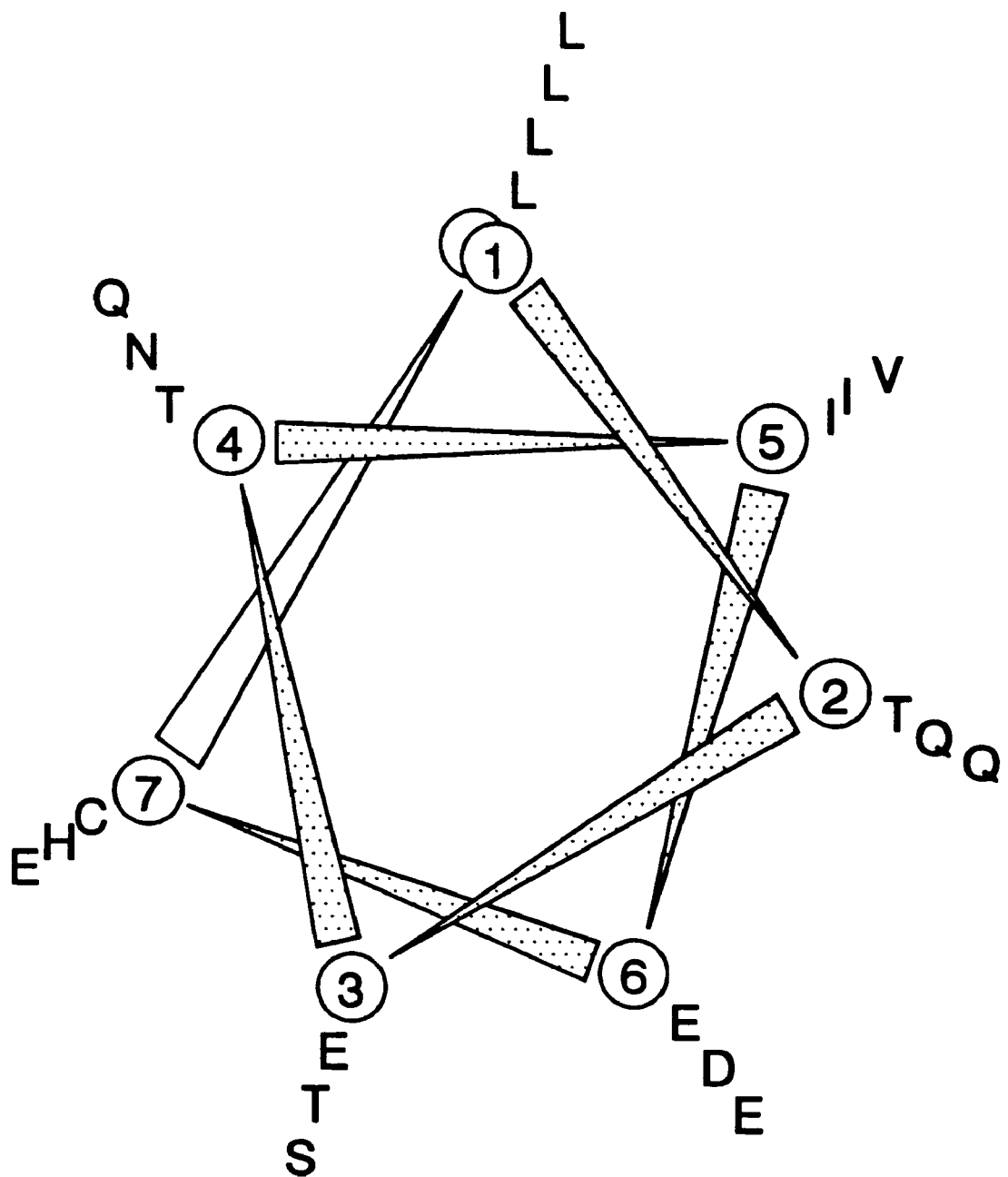

FIG. 6—Helical wheel analysis of leucine zipper domain. The analysis starts with leu (171) and ends at leucine (192). The helical wheel consists of seven spokes corresponding to the fit of seven amino acids into every two α helical turns. The single letter amino acid code is used.

FIGS. 7A–7D—cDNA (Seq. ID NO. 2) and amino acid sequence (Seq. ID NO. 1) of major Yo antigenic polypeptide of this invention.

DETAILED DESCRIPTION OF THE INVENTION

This invention provides an isolated nucleic acid sequence encoding major Yo paraneoplastic antigenic polypeptide. As used herein, the term major Yo paraneoplastic antigenic polypeptide encompasses any amino acid sequence having the biological activity of major Yo antigenic protein, i.e., a protein which may specifically form a complex with an antibody which is characteristic of paraneoplastic cerebellar degeneration. This antibody has also been called anti-Yo. This antibody, i.e., anti-Yo, is characteristically found in patients with paraneoplastic cerebellar degeneration, a disorder of the cerebellum found in association with neoplasms of lung and breast. This antigenic major Yo polypeptide is approximately 62 kd.

In one embodiment of this invention, the isolated nucleic acid sequence described hereinabove is DNA. In another embodiment of this invention, the isolated nucleic acid sequence described hereinabove is cDNA, or it is RNA. In the preferred embodiment of this invention, the isolated nucleic acid sequence is a cDNA sequence as shown in sequence ID No. 2, also FIGS. 7A–7D.

A vector which comprises the isolated nucleic acid molecule described hereinabove also is provided. Suitable vectors comprise, but are not limited to, a plasmid or a virus. This vector may be transfected into a suitable host cell to form a host vector system for the production of a polypeptide having the biological activity of the major Yo antigenic polypeptide.

This invention further provides an isolated DNA or cDNA molecule described hereinabove wherein the host cell is selected from the group consisting of bacteria cells such as *E. coli*, yeast and fungi cells, insect cells and animal cells. Suitable animal cells include, but are not limited to Vero cells, HeLa cells, Cos cells, CV1 cells and primary mouse cells.

Further provided by this invention is a method for producing a polypeptide having the biological activity of the major Yo antigenic polypeptide comprising the steps of: a) culturing the host vector system described hereinabove under suitable conditions permitting production of the polypeptide and b) recovering the polypeptide produced. This invention also provides the polypeptide produced by this method.

Throughout this application, references to specific nucleotides are to nucleotides present on the coding strand of the nucleic acid. The following standard abbreviations are used throughout the specification to indicate specific nucleotides:

C=cytosine A=adenosine
T=thymidine G=guanosine
U=uracil

This invention also encompasses DNAs and cDNAs which encode amino acid sequences which differ from those of the major Yo paraneoplastic antigenic polypeptide, but which should not produce phenotypic changes. Alternatively, this invention also encompasses DNAs and cDNAs which hybridize to the DNA and cDNA of the subject invention. Hybridization methods are well known to those of ordinary skill in the art. This invention also encompasses cDNA and DNA molecules characterized by changes in non-coding regions that do not alter the phenotype of the polypeptide produced.

Also provided by this invention is a purified, major Yo antigenic polypeptide. The purified major Yo antigenic polypeptide may be labeled with a detectable marker. For the purposes of this invention, suitable detectable markers include, but are not limited to detectable markers selected from the group consisting of radioisotopes, dyes, enzymes and biotin.

This invention further provides a monoclonal antibody directed to an epitope on the major Yo antigenic polypeptide. In one embodiment of this invention, the monoclonal antibody is a mouse monoclonal antibody. In another embodiment of this invention, the monoclonal antibody is a human monoclonal antibody.

For the isolation of mouse monoclonal antibodies, eight week old mice may be injected interperitoneally with about 50 micrograms of a synthetic, purified major Yo antigenic polypeptide, (prepared as described above) in complete Freud's adjuvant 1:1 volume. Mice will then be boosted, at monthly intervals, with the polypeptide, mixed with incomplete Freud's adjuvant, and bled through the tail vein. On days 4, 3, and 2 prior to fusion, mice will be boosted intravenously with 50 micrograms of the polypeptide in saline. Splenocytes will then be fused with non-secreting myeloma cells according to procedures which have been described and are known to those of ordinary skill in the art to which this invention pertains. Some time later, approximately two weeks later, hybridoma supernatant will then be screened for binding activity against the major Yo antigenic polypeptide as described hereinafter. Positive clones will then be isolated and propagated.

In addition, this invention also provides the monoclonal antibody described hereinabove conjugated to a therapeutic agent. For the purposes of this invention, suitable therapeutic agents include, but are not limited to, a therapeutic agent selected from the group consisting of radioisotopes, toxins, toxoids, and chemotherapeutic agents. Also provided by this invention is the monoclonal antibody described hereinabove conjugated to a detectable marker. Suitable detectable markers include, but are not limited to, enzymes, radioisotopes, dyes and biotin. This invention further provides monoclonal antibodies as described hereinabove conjugated to an imaging agent. Suitable imaging agents include, but are not limited to radioisotopes, such as, $^{32}P$, $^{35}S$, and $^{131}I$.

Also provided by this invention are pharmaceutical compositions comprising the purified, major Yo antigenic polypeptide described hereinabove alone, or conjugated to any one of the following: a detectable marker, a therapeutic agent, or an imaging agent, as described hereinabove and a pharmaceutically acceptable carrier. Further provided are pharmaceutical compositions comprising the monoclonal antibody described hereinabove alone, or conjugated to any one of the following: a detectable marker, a therapeutic agent, or an imaging agent. As used herein, the term "pharmaceutically acceptable carrier" encompasses any of the standard pharmaceutical carriers, such as phosphate buffered saline solution, water, emulsions, such as a oil/water emulsions, and various types of wetting agents.

A method of detecting an antibody associated with paraneoplastic cerebellar degeneration "PCD", i.e., the major Yo antigenic protein, is also provided by this invention. This method comprises contacting a suitable sample with a purified major Yo antigenic polypeptide described hereinabove under conditions so as to form a complex between the purified major Yo antigenic polypeptide and the antibody, detecting the presence of any complex so formed, thereby detecting an antibody associated with paraneoplastic cerebellar degeneration. Suitable samples include any sample suspected containing an antibody associated with PCD, such as serum or cerebral-spinal fluid. In one embodiment of the invention the synthetic purified major Yo antigenic polypeptide is labeled with a detectable marker selected from the group consisting of radioisotopes, dyes, enzymes and biotin. For the purposes of this invention, suitable radioisotopes include, but are not limited to, $^{32}P$, $^{35}S$, and $^{131}I$.

Also provided by this invention is a method of determining whether a patient exhibiting neurological symptoms harbors a tumor expressing the Yo antigen, which comprises obtaining the suitable sample from the patient, contacting the suitable sample with a monoclonal antibody directed against the Yo antigen, under conditions so as to form a complex between the antibody and the Yo antigen, detecting the presence of any complex so formed, the presence of a complex being a positive determination that the patient harbors a tumor expressing the Yo antigen. In one embodiment of this invention, the monoclonal antibody is labeled with a detectable marker. For the purposes of this invention, suitable detectable markers include, but are not limited to a detectable marker selected from the group consisting of radioisotopes, dyes, enzymes and biotin. Suitable radioisotopes have been described hereinabove.

Further provided by this invention is a method of inhibiting the proliferation of neoplastic cells in a patient having paraneoplastic cerebellar degeneration. This method comprises administering to the patient an effective amount of the monoclonal antibody or composition described hereinabove conjugated to a therapeutic agent, in an amount which is effective to inhibit the proliferation of neoplastic cells, and under suitable conditions so as to form a complex between an antigen associated with the neoplasm and the monoclonal antibody thereby inhibiting the proliferation of neoplastic cells. As used herein, an effective amount is any amount which is effective to inhibit the proliferation of neoplastic cells. As is known to those of ordinary skill in the art, effective amounts vary with the type of therapeutic agent utilized, as well the neoplastic cell tumor being treated. It is well known to those of ordinary skill in the art how to determine an effective amount of a suitable therapeutic agent.

As used herein, "administering" means a method of administering to the patient. Such methods are well known to those skilled in the art and include, but are not limited to administration orally, intravenously, or parenterally. Administration of the agent may be effected continuously or intermittently, such that the amount of the therapeutic agent in the patient is effective to inhibit proliferation of neoplastic cells. For the purposes of this invention suitable therapeutic agents include radioisotopes, toxins, toxoids, and chemotherapeutic agents.

Also provided by this invention is a method of imaging neoplastic cells in a patient, wherein the neoplastic cells are associated with paraneoplastic cerebellar degeneration.

The method comprises administering to the patient the monoclonal antibody described hereinabove which is labelled with an imaging agent, for example $^{131}I$, or a composition containing the same, and administered it to the patient to bind to a major Yo antigen present on or within the neoplastic cells so as to form a complex between the monoclonal antibody and the antigen, detecting any complex so formed, thereby imaging neoplastic cells in a patient associated with PCD, or neoplastic cells expressing Yo antigen. As is well known to those of ordinary skill in the art, a suitable amount of monoclonal antibody or composition is any amount which is effective to image the neoplastic cells, for example, about 0.1 mCi to about 50.0 mCi. In addition, an effective amount of the monoclonal antibody may be an amount from about 0.01 mg to about 100 mg. Suitable methods of administering the imaging agent are as described hereinabove.

Imaging of any complex so formed may be carried out using single photon computed emission tomography (SPECT) or by using a gamma camera.

Materials and Methods

Materials

Sera from patients with antibody associated paraneoplastic cerebellar degeneration was obtained from the patients' physicians. A Hela cell λ ZAP expression library was obtained from Stratagene.

Methods

Screening of A Hela Expression Library

Recombinant phage were screened at a density of $2 \times 10^4$ pfu per 150 mm plate of *E. coli* XLI-Blue. After incubation for 6 hours at 37° C. the plates were overlaid with filters soaked in 1PTG (10 mM) and incubated for a further 12 hours at 37° C. The filters were then removed and incubated with anti Yo sera (2 µg/ml IgG) for 2 hours at room temperature. The filters were then washed with TBST (50 mM Tris (pH 7.4), 100 mM NaCl, 0.2% Triton) and incubated with $I^{125}$ Protein A. After washing with TBST the filters were exposed to XRA5 film at −70° C. Clones yielding positive signals were purified by several rounds of antibody screening until 100% of the plaques gave positive signals.

Analysis of Fusion Proteins

Phage clones were subcloned into p Bluescript (pBs) using the phage rescue protocol. [10] Individual clones were grown to an optical density of 0.6 and induced by adding IPTG (10 mM). After 1 hour of induction at 37° C. the bacterial cells were isolated by centrifugation and lysed by the addition of 2% SDS Laemlli buffer. *E coli* lysates were then resolved by 8% polyacrylamide SDS gel electrophoresis and transferred to nitrocellulose [11]. The filters were then incubated with anti-Yo sera (5 µg/ml in TBST) for 2 hours at room temperature. The filters were then washed with TBST and incubated with $I^{125}$ protein A. After a further washing with TBST, the filters were exposed to XRA5 film at −70° C.

Northern Blot Analysis

Total RNA was prepared from Hela cells using the guanidinium hydrochloride phenol-chloroform extraction method. The RNA was separated by 1.2% Agarose/formaldehyde gel electrophoresis and transferred to Hybond N according to the manufacturers specification. The Hybond N filter was prehybridized with 50% Formamide, 5× SSPE, 0.05% PVP 0.05% Ficoll, 200 μg/ml denatured DNA. Probe was synthesized from clone pY2 using T7 RNA polymerase and $^{32}$P UTP. [10] The filter was hybridized with probe ($10^7$ cpm/ml) in prehybridization buffer at 55° C. The filter was then washed with 0.1× SSC/0.1% SDS at 60° C. and exposed to XRA5 film.

DNA Sequence Analysis

All sequencing was based on the dideoxy termination method [10]. Double stranded DNA was sequenced on both strands using SK, KS, M13 universal and reverse primers, and internal oligonucleotide primers. Sequences were merged and analyzed for open reading frame and functional motifs with the Macvector analysis software.

Elisa Assay

Partially purified preparations of the fusion protein encoded by pY2 were absorbed to 96 well microliter plates. After blocking reactive sites with 2% BSA/PBS, the wells were incubated with the appropriate concentration of sera diluted in 1% goat serum (2 hours at room temperature). Reactivity was determined by incubation with biotinylated goat anti-human IgG, (1/1000) followed by avidin-biotin peroxidase complex. Peroxidase was measured by oxidation of OPD and absorbance was measured at 402 nm.

Results

Isolation of Positive λ Clones

Figure 1:
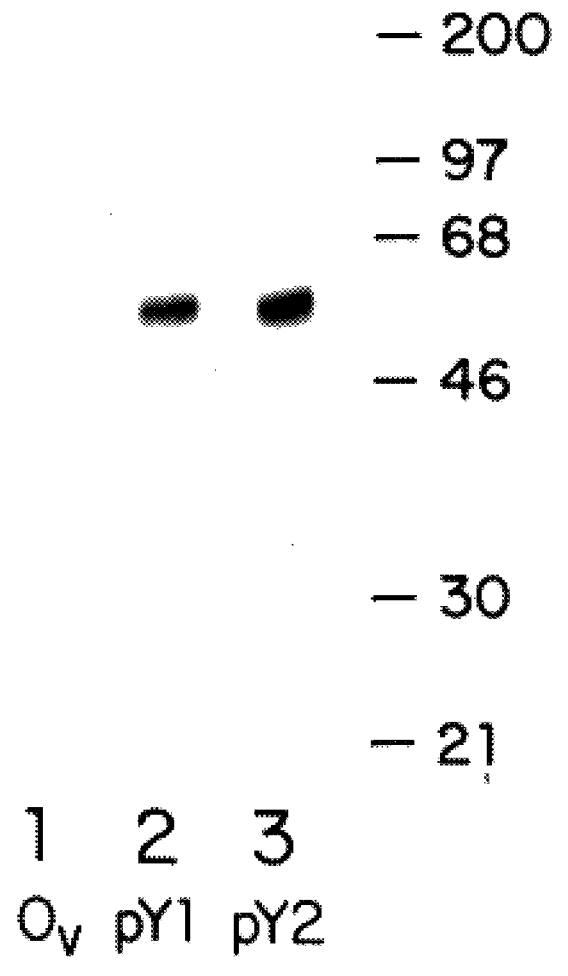

In order to clone the major Yo antigen (CDR 62) five libraries were obtained. Five were screened and found to be negative. Screening of a Hela cell λ ZAP II expression library with a typical high-titer anti-Yo sera resulted in the isolation of two consistently positive clones (y1,y2). None of these clones were recognized by normal human sera. The two clones were further analyzed by the epitope selection method. In this procedure, the antibodies that recognize the recombinant fusion protein are isolated and reacted with a Western blot of the tissue antigen. Purified antibodies from bona-fide clones should identify the original antigen of interest. FIG. 1 (lanes 3,4) shows that affinity purified antibodies selected by reactivity with the fusion proteins encoded by clones y1 and y2 recognized CDR 62 expressed in human Purkinje neurons. A mock purification of anti-Yo sera employing an irrelevant fusion protein served as the negative control (FIG. 1, lane 1). Both clones were related and encoded CDR 62.

Figure 2:
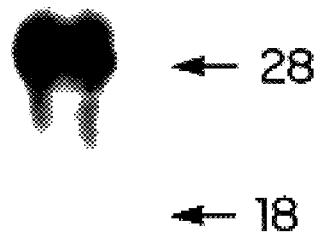
FIG. 2—Northern blot of HeLa RNA. Total RNA was extracted from HeLa cells and separated by 1.2% Formaldehyde-Agarose gel electrophoresis. The filter was incubated with [$^{32}$P] RNA probe, washed and exposed to XRA5 film for 4 hours at −70° C.

Both λ phage clones were then subcloned into PBS utilizing the phagemid rescue procedure. The resulting bacterial plasmids pY1, pY2 had inserts of 0.8 kb and 2.3 kb respectively. Restriction enzyme digestion and hybridization analysis confirmed that the two clones were related and overlapped. A similar antibody screen was conducted using a human cerebellar library. Four independent clones were isolated and found to be related to pY1 and pY2. These clones were not analyzed further. Northern blot analysis of Hela total RNA with probe synthesized from pY2 revealed an abundant transcript of 51K. (FIG. 2)

Specific Recognition of cDNA Clones by Anti-Yo Sera

Plasmid pY2 was deposited on Jan. 25, 1991 with the American Type Culture Collection (ATCC), 10801 University Boulevard, Manassas, Va. 20110-2209, U.S.A. under the provisions of the Budapest Treaty for the International Recognition of the Deposit of Microorganisms for the Purposes Of Patent Procedure. Plasmid pY2 has been accorded ATCC Accession Number 40948.

Figure 3A:
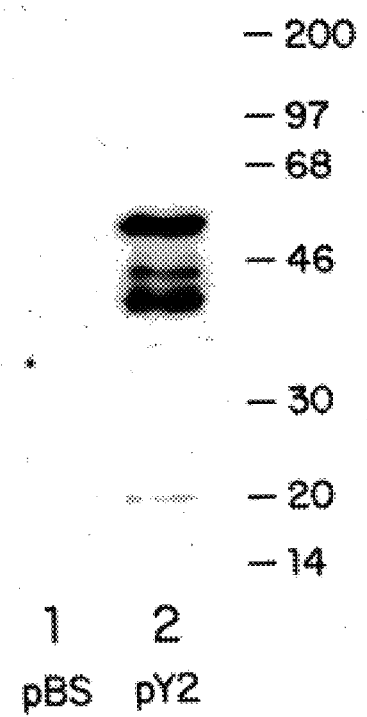
FIGS. 3A and 3B—Anti Yo sera specifically react with pY2 fusion protein.
Figure 3B:
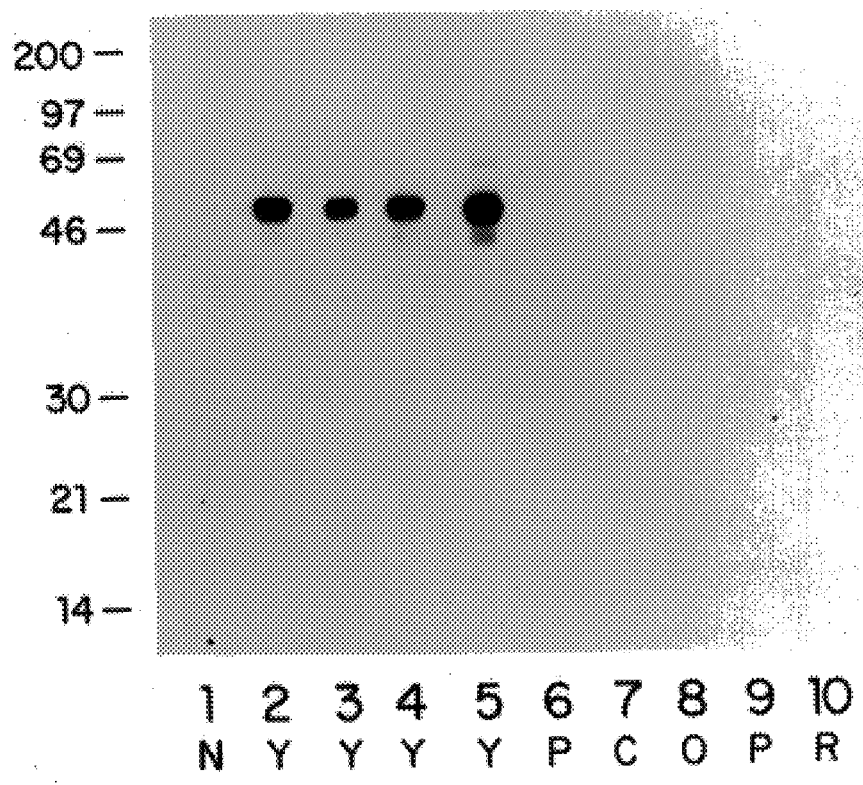

Preliminary experiments revealed that the fusion protein encoded by pY2 was the most reactive with anti-Yo sera. This clone was therefore the reagent of choice to establish a quantitative diagnostic assay. The reactivity of anti-Yo sera and various negative control sera was established by Western blot analysis of the fusion protein encoded by pY2. Anti-Yo sera identify a fusion protein of 55 kd in extracts of pY2. No reactivity was observed with extracts of PBS (the parental plasmid vector with no insert). (FIG. 3A, lane 2). FIG. 3B shows that reactivity with sera previously characterized as anti-Yo were positive (lanes 2,3,4,5,). Negative controls included; normal human sera (lane 1), sera from patients with cerebellar degeneration due to the causes (lane 7), patients with ovarian tumors (lane 8) and patients with ovarian tumors, PCD but no anti Yo antibody (lanes 6,9) and serum from a different antibody associated paraneoplastic syndrome (lane 10).

In a separate study, four false positive sera were distinguished by recombinant assay utilizing the antigen of the subject invention.

Elisa Assay for Anti-Yo Sera

The routine assay for the detection of anti-Yo antibodies involves immunohistochemical and Western blot analysis of human cerebellar tissue. Sera are defined as anti-Yo if they react specifically with Purkinje cells and identify a major species of 62 kd on Western blot analysis. Western blot analysis is essential since other sera which react with Purkinje cells but do not identify a 62 kd protein have been encountered. [12] This assay is currently conducted by research laboratories. Screening for this antibody in a large patient population will require a simpler diagnostic assay. Towards this end we have established an Elisa assay based on the recombinant CDR 62 antigen. Partially purified preparations of the pY2 fusion protein were immobilized on 96 well microliter plates and reacted with the same group of sera utilized in FIG. 3B. All four anti-Yo sera were clearly positive whereas all negative sera were not significantly different than background. (FIG. 4).

Sequence Analysis of pY1, pY2

Sequence analysis of pY2 revealed a large open reading frame of 431 amino acids which was in frame with the AUG of β galactosidase. The predicted molecular weight of this open reading frame (54 kd) agrees well with that observed in FIG. 3(A). Sequence analysis of pY1 confirmed that it overlapped with the 5' end of pY2 and provided another 243 nucleotides of 5' sequence. Together pY1 and pY2 yielded a composite open reading frame of 509 amino acids. (FIG. 5 Seq. I.D. No. 1). It has not yet been established that the N terminal AUG. Secondary structure analysis revealed a highly hydrophilic protein with extensive regions of α-Helix. The most conspicuous feature was a leucine zipper motif found at residues 171 to 192. This motif, consisting of a heptad repeat of leucine residues forming an amphiphillic α-Helix, is a distinctive feature of proteins which bind to DNA as a hetero or homodimer. [13, 14] The amphiphillic nature of the leucine zipper found in CDR62 is illustrated in a helical wheel analysis (FIG. 6). A thin ridge of hydrophobicity is evident down the axis of the putative α Helix. In addition allowing the substitution of serine (164) and histidine (137) a "super" leucine zipper stretches from residues 122 to 170 in complete register with the leucine zipper at 171 to 192. Helical wheel analysis of the "super" leucine zipper also revealed a clear hydrophobic ridge down the axis of the α Helix. Preliminary experiments have shown that CDR62 can in fact bind to DNA. Assaying CDR62 by Western blot we have shown that the protein present in cytoplasmic extracts of Hela cells binds strongly to native DNA-cellulose. (Fathallah & Furneaux, data not shown). CDR62 does not appear to contain the characteristic basic DNA binding domain found in many leucine zipper proteins. It should be noted however, the presence of two putative DNA binding motifs (a SPKK site (Seq. I.D. No. 3) at codon 201 and a Zinc Finger at codons 205–231) adjacent to the leucine zipper. Also consistent with the function of the protein as a transcription factor is the presence of a highly acidic (pI=3.4) activating domain between residues 52 and 80. Leucine zipper proteins in general display little homology in the amino acids found between the leucine residues. In this case it was noted that the almost perfect homology between a leucine zipper element found in CDR62 (LQTNIDHL-amino acids 178–185 of Seq. I.D. No. 1) to that found in the leucine zipper present in C-Fos [15] (LQTEIANL Seq. I.D. No. 4).

Discussion

A human expression library and isolated cDNA clones that encode an epitope recognized by the sera of patients were screened with antibody associated PCD. On the basis of the epitope selection analysis it has been concluded that these cDNAs correspond to the major antigen CDR62. There is a possibility that the cDNA's encode an epitope shared with CDR62 but do not correspond to the protein itself. Antibodies specifically raised against the fusion protein will definitively answer this question. Irrespective of the true identity of the cDNAs; they encode an antigenic species which is uniquely recognized by anti-Yo sera. In contrast to the previously cloned minor antigen (CDR34) the fusion proteins encoded by the present cDNAs are highly reactive with anti-Yo sera (detectable binding is observed at 0.2 μg/ml of IgG.). The fusion protein encoded by these clones, provides the most sensitive assay for the detection of anti-Yo sera.

The most conspicuous structural feature of CDR62 is a leucine zipper motif. The presence of this feature and of putative DNA binding domains is beleived to indicate that this protein plays a role in the regulation of gene expression. It will be crucial to isolate the DNA sequence recognized by CDR62. The similarity of the leucine zipper element between CDR62 and Cos. It is conceivable that CDR62 may interact with the same family of proteins that interact with C-Fos. [15] There is no obvious similarity between CDR62 and the previously cloned minor antigen CDR34. They are clearly different gene products, CDR34 resides on chromosome X (4) whereas CDR62 resides on chromosome X (4) whereas CDR62 resides on chromosome 16. CDR34 is an unusual protein consisting almost entirely of tandem repeats to a six amino acid consensus sequence L/FLEDVE (Seq. I.D. Nos. 5 and 6). Such tandem repetition gives rise to a number of single (L—L) zipper elements. We speculate that anti-Yo sera specifically recognizes leucine zipper elements. This speculation is fuelled by the recent isolation (from an expression library) of another gene product (CD III) which contains a leucine zipper element.

It is hypothesized that the pathological mechanisms of the syndrome is that cerebellar dysfunction arises from an immune response directed against the cerebellum but provoked by the aberrant expression of the neural antigen in tumor tissue. There is no direct proof of this model. Injection of anti-Yo antibodies into experimental animals have failed to reproduce the syndrome. The availability of the recombinant CDR62 antigen will permit the generation of an appropriate immune response in experimental animals and hopefully create an animal model. In addition, the specific expression of CDR62 in patient's tumor samples can now be examined. The other fascinating aspect of this syndrome is that these patients made an extremely exaggerated immune response to their tumor tissue. Tumor tissue (presumably the CDR62 antigen) is clearly perceived as foreign by the patient's immune system. There are at least two models which may help us to understand this phenomenon. Firstly it may be that the CDR62 protein are normally restricted in its expression to brain tissue. The brain is an immunologically privileged site. [16, 17] The implication is that the expression of a brain protein in extra-neural tumor tissue may provoke an intense immune response. In the second model we suggest that the CDR62 antigen is expressed normally in extra-neural tissue but it undergoes a somatic mutation. In view of the highly hydrophilic a helical structure of CDR62, it is reasonable to suppose that even a single amino acid change may drastically affect the structure of the protein. The abnormal epitopes thus created may result in CDR62 being perceived as foreign by the immune system. An underlying corollary is that the mutation in CDR62 would have to be a clonal event. This would imply that mutation in CDR62 is a necessary event for tumor progression. With the cloned CDR62 in hand these models can now be tested.

REFERENCES

1. Henson, R. and Urich, H. "Cancer and the nervous system." 1982 Blackwell Scientific. Oxford.
2. Brain, L. and Wilkinson, M. 88: 465–478, 1965.
3. Furneaux, H. and Posner, J. Paraneoplastic neurological syndromes. Proc. Assoc. Res. Nerv. Men. Dis. 68: 187219, 1990.
4. Anderson, N. E., Rosenblum, M. K., Graus, F., Wiley, R. G. and Posner, J. B. Autoantibodies in paraneoplastic syndromes associated with small-cell lung cancer. Neurology 38: 1391–1398, 1988.
5. Furneaux, H., Rosenblum, M., Dalmau, J., Wong, E., Woodruff, P., Graus, F. and Posner, J. Selective expression of Purkinje cell antigens in tumor tissue from patients with paraneoplastic cerebellar degeneration. New Eng. J. Med. 322: 1844–51, 1990.
6. Furneaux, H., Reich, L. and Posner, J. Central nervous system synthesis of autoantibodies in paraneoplastic syndromes. Neurology. 40: 1085–1091, 1990.
7. Cunningham, J., Graus, F., Anderson, N. and Posner, J. Partial characterization of the Purkinje cell antigens in paraneoplastic cerebellar degeneration. Neurol. 36: 1163–1168, 1986.
8. Dropcho, E., Chen, Y., Posner, J. and Old, L. Cloning of a brain protein identified by autoantibodies from a patient with paraneoplastic cerebellar degeneration. Proc. Nat. Acad. Sci. 84: 1987.
9. Furneaux, H., Dropcho, E., Barbut, D., Chen, Y. -T., Rosenblum, M., Old, L. and Posner, J. Characterization of a cDNA encoding a 34 kd Purkinje neuron protein recognized by sera from patients with paraneoplastic cerebellar degeneration. Proc. Natl. Acad. Sci, U.S.A. 86: 2873–2877, 1989.
10. Maniatis, T., Fritsch, B. and Sambrook, J. "Molecular cloning: a laboratory manual." 1982 Cold Spring Harbor, New York.
11. Towbin, H., Staehelin, T. and Gordon, J. A procedure for the electrophoretic transfer of proteins from polyacrylamide gels to nitro cellulose sheets. Proc. Nat. Acad. Sci. 76: 4350–4352, 1979.
12. Darnell, R., Furneaux, H. and Posner, J. Characterization of neural antigens recognized by autoantibodies in CSF and serum of a patient with cerebellar degeneration: co-expression in Purkinje cells and tumor lines of neuro-ectodermal origin. Neurology. 39(Suppl.1): 385, 1989.
13. Landschulz, W., Johnson, P. and McKnight, S. Science. 240: 1759, 1988.
14. Vinson, C., Sigler, P. and McKnight, S. Scissors-grip model for DNA recognition by a family of leucine zipper proteins. Science. 246: 911–916, 1989.
15. Gentz, R., Rauscher, F. I., Abate, C. and Curran, T. Science. 243: 1695–1699, 1989.
16. Lampson, L. Molecular bases of the immune response to neural antigens. Trends Neurosci. 10: 211–6, 1987.
17. Medawar, P. Immunity to homologous grafted skin III the fate of skin homografts transplanted to the brain, to subcutaneous tissue, and to the anterior chamber of the eye. Br. J. Exp. Pathol. 29: 58–69, 1948.
18. Sakai, K. et al. Isolation of a complementary DNA clone encoding an autoantigen recognized by an anti-neuronal cell antibody from a patient with paraneoplastic cerebellar degeneration. Annals of Neurology, 28 (5): 692–698, 1990.
19. Anderson, N. E. et al. Paraneoplastic cerebellar degeneration: clinical-immunological correlations, Annals of Neurology, 24 (4): 559–567, 1988.

What is claimed is:

1. A method of detecting an antibody associated with paraneoplastic cerebellar degeneration (PCD) which comprises contacting a suitable sample with a fusion protein designated Y2 and expressed by the plasmid pY2 (ATCC Accession No. 40948) under conditions so as to form a complex between the fusion protein and the antibody, detecting the presence of any complex so formed, thereby detecting the antibody associated with paraneoplastic cerebellar degeneration.

2. The method of claim 1, wherein the fusion protein is labeled with a detectable marker.

3. The method of claim 2, wherein the detectable marker is a radioisotope, dye, enzyme or biotin.

4. A method of determining whether a patient exhibiting neurological symptoms harbors a tumor expressing major Yo antigen which comprises:

(a) obtaining a fusion protein designated Y2 which is expressed by plasmid pY2 (ATCC Accession No. 40948);

(b) raising an antibody against the fusion protein obtained in step (a) and isolating said raised antibody;

(c) contacting a suitable sample from the patient with the isolated antibody from step (b) under suitable conditions so as to form a complex between the isolated antibody and the major Yo antigen; and (d) detecting the presence of any complex so formed, the presence of complex indicating that the patient harbors a tumor expressing major Yo antigen.

5. The method of claim 4, wherein the isolated antibody is labeled with a detectable marker.

6. The method of claim 5, wherein the detectable marker is a radioisotope, dye, enzyme or biotin.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 509 amino acids
      (B) TYPE: amino acid
      (C) STRANDEDNESS: single
      (D) TOPOLOGY: linear (ii) MOLECULE TYPE: peptide (iii) HYPOTHETICAL: N (iv) ANTI-SENSE: N (v) FRAGMENT TYPE: N-terminal (vii) IMMEDIATE SOURCE:
      (A) LIBRARY: Hela cell library
      (B) CLONE: pY1pY2

(xi) SEQUENCE DESCRIPTION: SEQ ID NO:1:

```
Ser Ala Ala Gly Pro Asn Gly Ala Glu Ala Ala Gln Arg Ser Leu Gly
 1               5                  10                  15

Gly Gly Ala Ser Arg Pro Arg Ala Ala Leu Ala Glu Gly Gly Gly Ala
                20                  25                  30

Gly Glu Glu Pro Gly Ala Ala Ala Glu Ala Gly Arg Arg Arg Gly Pro
            35                  40                  45

Leu Pro Leu Glu Asp Pro Ala Glu Met Leu Ala Glu Asn Leu Val Glu
    50                  55                  60

Glu Phe Glu Met Lys Glu Asp Glu Pro Trp Tyr Asp His Gln Asp Leu
65                  70                  75                  80

Gln Gln Asp Leu Gln Leu Ala Ala Glu Leu Gly Lys Thr Leu Leu Asp
                85                  90                  95

Arg Asn Thr Glu Leu Glu Asp Ser Val Gln Gln Met Tyr Thr Thr Asn
                100                 105                 110

Gln Glu Gln Leu Gln Glu Ile Glu Tyr Leu Thr Lys Gln Val Glu Leu
            115                 120                 125

Leu Arg Gln Met Asn Glu Gln His Ala Lys Val Tyr Glu Gln Leu Asp
        130                 135                 140

Val Thr Ala Arg Glu Leu Glu Glu Thr Asn Gln Lys Leu Val Ala Asp
145                 150                 155                 160

Ser Lys Ala Ser Gln Gln Lys Ile Leu Ser Leu Thr Glu Thr Ile Glu
                165                 170                 175
```

```
            Cys Leu Gln Thr Asn Ile Asp His Leu Gln Ser Gln Val Glu Glu Leu
                        180                 185                 190

Lys Ser Ser Gly Gln Gly Arg Arg Ser Pro Gly Lys Cys Asp Gln Glu
                        195                 200                 205

Lys Pro Ala Pro Ser Phe Ala Cys Leu Lys Glu Leu Tyr Asp Leu Arg
                        210                 215                 220

Gln His Phe Val Tyr Asp His Val Phe Ala Glu Lys Ile Thr Ser Leu
            225                 230                 235                 240

Gln Gly Gln Pro Ser Pro Asp Glu Glu Asn Glu His Leu Lys Lys
                        245                 250                 255

Thr Val Thr Met Leu Gln Ala Gln Leu Ser Leu Glu Arg Gln Lys Arg
                        260                 265                 270

Val Thr Met Glu Glu Glu Tyr Gly Leu Val Leu Lys Glu Asn Ser Glu
                        275                 280                 285

Leu Glu Gln Gln Leu Gly Ala Thr Gly Ala Tyr Arg Ala Arg Ala Leu
                        290                 295                 300

Glu Leu Glu Ala Glu Val Ala Glu Met Arg Gln Met Leu Gln Ser Glu
            305                 310                 315                 320

His Pro Phe Val Asn Gly Val Glu Lys Leu Val Pro Asp Ser Leu Tyr
                        325                 330                 335

Val Pro Phe Lys Glu Pro Ser Gln Ser Leu Leu Glu Glu Met Phe Leu
                        340                 345                 350

Thr Val Pro Glu Ser His Arg Lys Pro Leu Lys Arg Ser Ser Ser Glu
                        355                 360                 365

Thr Ile Leu Ser Ser Leu Ala Gly Ser Asp Ile Val Lys Gly His Glu
                        370                 375                 380

Glu Thr Cys Ile Arg Arg Ala Lys Ala Val Lys Gln Arg Gly Ile Ser
            385                 390                 395                 400

Leu Leu His Glu Val Asp Thr Gln Tyr Ser Ala Leu Lys Val Lys Tyr
                        405                 410                 415

Glu Glu Leu Leu Lys Lys Cys Gln Glu Glu Gln Asp Ser Leu Ser His
                        420                 425                 430

Lys Ala Gly Arg Pro Pro Gly Cys Ser Gln Gly Pro Asp Trp Ser Asp
                        435                 440                 445

Ala Gln Ser Glu Pro Val Ala Ser Gly Trp Glu Leu Ala Ser Val Asn
                        450                 455                 460

Pro Glu Pro Val Ser Ser Pro Thr Thr Pro Pro Glu Tyr Lys Ala Leu
            465                 470                 475                 480

Phe Lys Glu Ile Phe Ser Cys Ile Lys Lys Thr Lys Gln Glu Ile Asp
                        485                 490                 495

Glu Gln Arg Thr Lys Tyr Arg Ser Leu Ser Ser His Ser
                        500                 505

(2) INFORMATION FOR SEQ ID NO:2:

(i) SEQUENCE CHARACTERISTICS:
           (A) LENGTH: 2333 base pairs
           (B) TYPE: nucleic acid
           (C) STRANDEDNESS: single
           (D) TOPOLOGY: linear (ii) MOLECULE TYPE: cDNA (iii) HYPOTHETICAL: N (iv) ANTI-SENSE: N (vii) IMMEDIATE SOURCE:
```

(B) CLONE: Py2

(xi) SEQUENCE DESCRIPTION: SEQ ID NO:2:

```
TCCCCGCAAG ATCTTCAACT TGCTGCTGAG CTTGGGAAGA CATTACTGGA TCGGAACACA         60

GAGTTGGAGG ACTCTGTTCA GCAGATGTAT ACAACCAATC AGGAGCAGTT ACAGGAAATT        120

GAGTATCTGA CGAAGCAAGT GGAACTTCTA CGGCAGATGA ACGAACAACA TGCAAAGGTT        180

TATGAACAAT TAGACGTCAC AGCAAGGGAA CTGGAAGAAA CAAATCAAAA GCTAGTTGCT        240

GACAGCAAGG CCTCACAGCA AAAGATTCTG AGCCTGACTG AAACGATTGA ATGCCTGCAA        300

ACCAACATTG ATCACCTCCA GAGCCAAGTG GAGGAGCTGA AGTCATCTGG CCAAGGGAGA        360

AGGAGCCCGG GAAAGTGTGA CCAGGAGAAA CCGGCACCCA GCTTTGCATG TCTGAAGGAG        420

CTGTATGACC TCCGCCAACA CTTCGTGTAT GATCATGTGT TCGCTGAGAA GATCACTTCC        480

TTGCAAGGTC AGCCAAGCCC TGATGAAGAG GAAAATGAGC ACTTGAAAAA AACAGTGACA        540

ATGTTGCAGG CCCAGCTGAG CCTGGAGCGG CAGAAGCGGG TGACTATGGA GGAGGAATAT        600

GGGCTCGTGT TAAAGGAGAA CAGTGAACTG GAGCAGCAGC TGGGGGCCAC AGGTGCCTAC        660

CGAGCACGGG CGCTGGAACT AGAGGCCGAG GTGGCAGAGA TGCGACAGAT GTTGCAGTCA        720

GAGCATCCAT TTGTGAATGG AGTTGAGAAG CTGGTGCCAG ACTCTCTGTA TGTTCCTTTC        780

AAAGAGCCCA GCCAGAGCCT GCTGGAAGAG ATGTTCCTGA CTGTGCCGGA ATCACATAGA        840

AAGCCTCTCA AGCGCAGCAG CAGTGAGACG ATCCTCAGCA GCTTGGCAGG GAGTGACATC        900

GTGAAGGGCC ACGAGGAGAC CTGCATCAGG AGGGCCAAGG CTGTGAAACA GAGGGGCATC        960

TCCCTTCTGC ACGAAGTGGA CACGCAGTAC AGCGCCCTGA AGGTGAAGTA TGAAGAGTTG       1020

CTGAAGAAGT GCCAAGAGGA ACAGGACTCC CTGTCACACA AGGCTGGCAG ACCTCCAGGC       1080

TGCAGCCAAG GACCTGACTG GAGTGACGCC CAGTCTGAGC CTGTTGCCAG CGGCTGGGAA       1140

CTGGCCTCTG TCAACCCAGA GCCCGTGAGT TCCCCTACAA CACCTCCAGA ATACAAAGCG       1200

TTGTTTAAGG AGATCTTTAG TTGCATCAAG AAAACTAAGC AGGAAATAGA TGAACAGAGA       1260

ACAAAATACC GATCACTCTC CTCTCATTCT TAATTGACCT CTAGCTCTAC TACTAATTTG       1320

CCTATTGCCT ATCGCCTCTC TCCCATTCAG ACAAGTGTTT GTAGACTCTG AAGCCTAATG       1380

TTACTCATGA CGTTTGCCTC ATTGCTTTGC TTATTTAGCA AATGCATACA ACGAGGAAAG       1440

GAGGTGGCTA GTGGTATCAG TTCTCTGATC CACTTCCATT TAACCTCCCC AGGAAATCCC       1500

ATGACAAACT GGCCTCTGGC TGGCGCGCTG ATTAGACTTC AGTTCCTGAA AAGGACCAGT       1560

GGAGGGAAGA GCTATACTTC TGGAGAAGTA GGCCTGGAGT TACTACAGTA TGGGGGAAAA       1620

GGGTCGAGTT AGAACAAAGC TAAGGCAATT CCTATTGCTT CCTTGCGCAA CTTCTCAAAA       1680

CGATGAAAGT CAGAAGGCTG TCAAACTCAA ATATCTTTGC AAACACTGTT TGAATACTGT       1740

GAATTCTTCA TTACGAAGAA TGTTCGAGAG AAAGCAGGGG TCTAATCCAA AAGAAATGTC       1800

ATTAACCAAT ACTCCAAGTC CTTGAGTTTT GTTATATCTG AACTAGTTGA ACTGTGACTG       1860

ACAGGTAATC CTAATATATC CAAATCCAAC TGAATACCAA ATTGAGATGG CAAATTTTTG       1920

TTTGATATAA GTTAGCTTGT TAGCATATGC CCTAGAGGGC CTCCATCCCT GATTCTAATG       1980

TTTTTACTCA AAGCTCTAGC CTTTAGGATA GGTGAATATG TAAATCTTTT ATCACTTTCT       2040

CAAATTCAAA CTAAAGGGGA AAGATCAAAC CCCTTCCCTT CCTACCTGTT TTCTGAGCTG       2100

GCTGACTTGC CAGCCACAAG CTGCTCTTGC AGAGTTCTTA CCATTCCTGT AAATGTTTTG       2160

ACTTGTTGCA GAAATTCCTA TCTACTTTAT TAAGCAGTAT TGATCTGACT GTGGAAACAT       2220

CCTCTCACTT GCATTCTTTT AACTTAAAAC TATTTAAGAA CTGATGTTCC GATTATTGTA       2280
```

TATATTTTTC TAAAAACCAA ATAAAGCTAC CTATGAAAGG AATTCCGGAA TTC            2333

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:3:

Ser Pro Lys Lys
    1

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:4:

Leu Gln Thr Glu Ile Ala Asn Leu
    1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:5:

Leu Leu Glu Asp Val Glu
    1               5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:6:

```
Phe Leu Glu Asp Val Glu
 1               5
```

(2) INFORMATION FOR SEQ ID NO:7:

(i) SEQUENCE CHARACTERISTICS:
        (A) LENGTH: 430 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:7:

```
Ser Pro Gln Asp Leu Gln Leu Ala Ala Glu Leu Gly Lys Thr Leu Leu
 1               5                  10                  15

Asp Arg Asn Thr Glu Leu Glu Asp Ser Val Gln Gln Met Tyr Thr Thr
             20                  25                  30

Asn Gln Glu Gln Leu Gln Glu Ile Glu Tyr Leu Thr Lys Gln Val Glu
         35                  40                  45

Leu Leu Arg Gln Met Asn Glu Gln His Ala Lys Val Tyr Glu Gln Leu
     50                  55                  60

Asp Val Thr Ala Arg Glu Leu Glu Thr Asn Gln Lys Leu Val Ala
65                  70                  75                  80

Asp Ser Lys Ala Ser Gln Gln Lys Ile Leu Ser Leu Thr Glu Thr Ile
                 85                  90                  95

Glu Cys Leu Gln Thr Asn Ile Asp His Leu Gln Ser Gln Val Glu Glu
                100                 105                 110

Leu Lys Ser Ser Gly Gln Gly Arg Arg Ser Pro Gly Lys Cys Asp Gln
            115                 120                 125

Glu Lys Pro Ala Pro Ser Phe Ala Cys Leu Lys Glu Leu Tyr Asp Leu
        130                 135                 140

Arg Gln His Phe Val Tyr Asp His Val Phe Ala Glu Lys Ile Thr Ser
145                 150                 155                 160

Leu Gln Gly Gln Pro Ser Pro Asp Glu Glu Asn Glu His Leu Lys
                165                 170                 175

Lys Thr Val Thr Met Leu Gln Ala Gln Leu Ser Leu Glu Arg Gln Lys
                180                 185                 190

Arg Val Thr Met Glu Glu Glu Tyr Gly Leu Val Leu Lys Glu Asn Ser
            195                 200                 205

Glu Leu Glu Gln Gln Leu Gly Ala Thr Gly Ala Tyr Arg Ala Arg Ala
        210                 215                 220

Leu Glu Leu Glu Ala Glu Val Ala Glu Met Arg Gln Met Leu Gln Ser
225                 230                 235                 240

Glu His Pro Phe Val Asn Gly Val Glu Lys Leu Val Pro Asp Ser Leu
                245                 250                 255

Tyr Val Pro Phe Lys Glu Pro Ser Gln Ser Leu Leu Glu Glu Met Phe
                260                 265                 270
```

```
Leu Thr Val Pro Glu Ser His Arg Lys Pro Leu Lys Arg Ser Ser Ser
        275             280             285

Glu Thr Ile Leu Ser Ser Leu Ala Gly Ser Asp Ile Val Lys Gly His
    290             295             300

Glu Glu Thr Cys Ile Arg Arg Ala Lys Ala Val Lys Gln Arg Gly Ile
305             310             315                     320

Ser Leu Leu His Glu Val Asp Thr Gln Tyr Ser Ala Leu Lys Val Lys
                325             330             335

Tyr Glu Glu Leu Leu Lys Lys Cys Gln Glu Glu Gln Asp Ser Leu Ser
            340             345             350

His Lys Ala Gly Arg Pro Pro Gly Cys Ser Gln Gly Pro Asp Trp Ser
        355             360             365

Asp Ala Gln Ser Glu Pro Val Ala Ser Gly Trp Glu Leu Ala Ser Val
    370             375             380

Asn Pro Glu Pro Val Ser Ser Pro Thr Thr Pro Pro Glu Tyr Lys Ala
385             390             395             400

Leu Phe Lys Glu Ile Phe Ser Cys Ile Lys Lys Thr Lys Gln Glu Ile
            405             410             415

Asp Glu Gln Arg Thr Lys Tyr Arg Ser Leu Ser Ser His Ser
            420             425             430
```